United States Patent [19]

Asselin et al.

[11] 4,044,131

[45] Aug. 23, 1977

[54] 2-MORPHOLINOL DERIVATIVES

[75] Inventors: Andre A. Asselin, Ville le Moyne; Leslie G. Humber, Dollard des Ormeaux, both of Canada

[73] Assignee: American Home Products Corporation, New York, N.Y.

[21] Appl. No.: 634,685

[22] Filed: Nov. 24, 1975

[51] Int. Cl.$^2$ .................. C07D 265/32; A61K 31/535
[52] U.S. Cl. ........................... 424/248.58; 260/570.7; 544/174; 544/134; 544/82; 544/143; 544/163; 544/165; 544/168
[58] Field of Search ................. 260/247.7 S, 247.7 Z; 424/248, 248.58

[56] References Cited

U.S. PATENT DOCUMENTS

| | | | |
|---|---|---|---|
| 3,857,839 | 12/1974 | Lee | 260/247.7 S |
| 3,959,273 | 5/1976 | Mallion et al. | 260/247.7 S |

Primary Examiner—Henry R. Jiles
Assistant Examiner—R. W. Ramsuer
Attorney, Agent, or Firm—Arthur E. Wilfond

[57] ABSTRACT

2-Morpholinol derivatives characterized by having an aryloxymethyl radical attached to the 6 position and an alkyl or alkynyl radical attached to the nitrogen at the 4 position are disclosed. The derivatives may be optionally substituted at the 2 position with an alkyl or aryl group and the hydroxyl function at position 2 may be replaced with an alkoxy group. The 2-morpholinol derivatives of this invention are useful β-adrenergic blocking and antifungal agents. Methods for the preparation and use of these derivatives are also described.

8 Claims, No Drawings

2-MORPHOLINOL DERIVATIVES

BACKGROUND OF THE INVENTION

1. Field of the Invention

This invention relates to novel 2-morpholinol derivatives, to processes for their preparation, to intermediates used for the processes, to methods for using the 2-morpholinol derivatives and to pharmaceutically acceptable compositions of said derivatives.

More specifically, the present invention relates to novel 2-morpholinol derivatives possessing valuable pharmacologic properties. For example, these derivatives exhibit useful β-adrenergic blocking and antifungal properties at dosages which do not elicit undesirable side effects. The combination of these pharmacologic properties together with a lower order of toxicity render the 2-morphinols of the invention therapeutically useful.

2. Description of the Prior Art

Only a rather limited number of reports dealing with 2-morpholinol derivatives are available. A typical report describes 2-morpholinol derivatives, namely a number of substituted 2-hydroxy-2-(3', 4'-dihydroxyphenyl) morpholine derivatives, see H. Langecker and H. Freibel, Naunyn-Schmeidebergs Arch. exptl. Pathol. Pharmakol. 226, 493–504(1955) (C.A.50: 2061 i). However in this reference the 2-morpholinols are substituted at the 2 position with a dihydroxyphenyl group whereas the compounds of this invention are substituted at the 6 position with an aryloxymethyl group. Only recently derivatives of aryloxymethyl-morpholines have been prepared by S.A. Lu, U.S. Pat. No. 3,857,839, issued Dec. 31, 1974 and D.T. Arunwood et al., J. Med. Chem., 18, 573(1975). The latter compounds are distinguished readily from the compounds of the present invention by lacking the hydroxy function on the morpholine ring.

SUMMARY OF THE INVENTION

The compounds of this invention are represented by formula I.

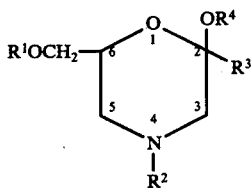

in which $R^1$ is 1-naphthalenyl; $R^2$ is selected from the group consisting of lower alkyl and lower alkynyl; $R^3$ is selected from the group consisting of hydrogen, lower alkyl, phenyl and phenyl substituted with a halo; and $R^4$ is selected from the group consisting of hydrogen and lower alkyl.

Also included are the therapeutically acceptable acid addition salts of the compounds of formula I.

The 2-morpholinol derivatives of this invention of formula I in which $R^1$, $R^2$ and $R^3$ are as defined herein and $R^4$ is hydrogen are prepared by a process comprising:

condensing a compound of formula II $$R^1OCH_2CH(OH)CH_2NHR^2 \qquad (II)$$

in which $R^1$ and $R^2$ are as defined herein with a compound of formula III,

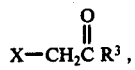

in which $R^3$ is as defined herein and X is a halogen selected from the group consisting of chlorine, bromine and iodine, in the presence of an alkali metal base to obtain said corresponding compound of formula I in which $R^1$, $R^2$ and $R^3$ are as defined herein and $R^4$ is hydrogen.

Alternatively, the compounds of this invention of formula I are prepared by a process comprising:

condensing a compound of formula II in which $R^1$ and $R^2$ are as defined herein with a compound of formula IV, $$XCH_2C(OR^5)_2R^3 \qquad (IV),$$

in which $R^3$ is as defined herein, $R^5$ is lower alkyl and X is a halogen selected from the group consisting of chlorine, bromine and iodine, in the presence of an alkali metal base to obtain the corresponding compound of formula V, $$R^1OCH_2CH(OH)CH_2N(R^2)CH_2C(OR^5)_2R^3 \qquad (V),$$

in which $R^1$, $R^2$, $R^3$ and $R^5$ are as defined herein and treating said last-named compound with a mineral acid to obtain the corresponding compound of formula I in which $R^1$, $R^2$, $R^3$ and $R^4$ are as defined herein. More particularly, treating said compound of formula V with a mineral acid under anhydrous conditions gives the corresponding compound of formula I in which $R^4$ is lower alkyl or alternatively treating said compound of formula V with a mineral acid, in the presence of water gives the corresponding compound of formula I in which $R^4$ is hydrogen.

The compounds of this invention of formula I, or a therapeutically acceptable salt thereof, exhibit a high degree of activity on β-receptors. More particularly, they are β-adrenergic blocking agents and are useful in the treatment of heart diseases such as angina pectoris, cardiac arrhythmias, hypertrophic subaortic stenosis and pheochromocytoma. The compounds of this invention of formula I, or a pharmaceutically acceptable salt thereof, are also useful for treating fungal infections in a mammal. Pharmaceutical compositions of these compounds are included as another aspect of this invention.

DETAILED DESCRIPTION OF THE INVENTION

The term "lower alkyl" as used herein contemplates both straight and branched chain alkyl radicals containing from one to six carbon atoms and includes methyl, ethyl, propyl, isopropyl, butyl, isobutyl, 2-methylpentyl and the like.

The term "lower alkynyl" as used herein contemplates both straight and branched chain alkynyl radicals containing from two to six carbon atoms and includes ethynyl, 2-propynyl, 1,1-dimethyl-2-propynyl and the like.

The term "halo or halogen" as used herein contemplates halogens and includes fluorine, chlorine, bromine and iodine unless stated otherwise.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, ether or an ethanol-ether mixture. These salts, when administered to mammals, possess the same pharmacologic activities as the corresponding bases. For many purposes it is preferable to administer the salts rather than the base compounds. Examples of salts are those with organic acids, e.g. acetic, lactic, succinic, benzoic, salicyclic, methanesulfonic or toluenesulfonic acid, as well as polymeric acids such as tannic acid or carboxymethyl cellulose, and salts with inorganic acids, for instance, phosphoric acid, sulfuric acid or a hydrohalic acid, e.g., hydrochloric acid. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

Also included in this invention are the stereochemical isomers of the compounds of formula I which result from asymmetric centers, contained therein.

β-ADRENERGIC BLOCKING ACTIVITY

The compounds of formula I or their acid addition salts thereof with therapeutically acceptable acids have particular usefulness as β-adrenergic blocking agents and are thus useful in the treatment of heart diseases such as angina pectoris, hypertrophic subaortic stenosis, pheochromocytoma and cardiac arrhythmias. For example representative experiments in anesthesized rats, the preferred compounds, 2-(p-chlorophenyl)-4-isopropyl-6-[1-(naphthalenyloxymethyl)]-2-morpholinol hydrochloride (Example 1) and 4-isopropyl-2-methyl-6-[1-(naphthalenyloxymethyl)]-2-morpholinol p-toluenesulfonate (Example 2), inhibit the depressor responses to isoproterenol and potentiate the pressor responses to epinephrine at oral doses of 300 and 50 mg/Kg respectively. Furthermore, the latter compounds exhibit effects characteristic of β-adrenergic blockers by possessing hypotensive activity, which is demonstrable in standard pharmacological tests. For example, in tests conducted in the spontaneously hypertensive rat (SHR) such as described by R. Tabei, et al., Clin. Pharmacol, Therap., 11,269 (1970) or J. Vavra, et al., Can. J. Physiol. Pharmacol., 51, 727 (1973). More specifically exemplified, a testing method such as described in the latter publication shows that the latter described preferred compounds cause a notable blood pressure decrease in the SHR at about four hours after a dose of 50 - 150 mg/kg/perorally.

When the compounds of formula I or this invention are used as β-receptor blocking agents in mammals e.g. rats, dogs and mice, they are used alone or in combination with pharmacologically acceptable carriers, the proportion of which is determined by the solubility and chemical nature of the compound, chosen route of administration and standard biological practice. For example, they are administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the 2-morpholinol derivatives of this invention will vary with the form of administration and the particular compound chosen. Furthermore, it will vary with the particular host as well as the age and condition of the host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects. The effective β-receptor blocking amount of the compounds usually ranges from about 1.0 mg to about 500 mg per kilo per day, although as aforementioned variations will occur. However a dosage level that is in the range of from about 10 mg to about 300 mg per kilo per day is employed most desirably in order to achieve effective results.

ANTIFUNGAL ACTIVITY

The compounds of formula I or their acid addition salts thereof with pharmaceutically acceptable acids also exhibit utility as antifungal agents against a number of pathogenic fungi, for example, *Candida albicans* and *Trichophyton granulosum*, in standard tests for antifungal activity, such as those described in "Antiseptics, Disinfectants, Fungicides and Sterilization," G. F. Reddish, Ed., 2nd ed., Lea and Febiger, Philadelphia, 1957 or by D. C. Grove and W. A. Randall in "Assay Methods of Antibiotics," Med. Encycl. Inc., New York, 1955.

For example, by employing a test like the serial broth dilution, see Grove and Randall, cited above, in which dilutions of the compounds of this invention in nutrient broth are inoculated with the fungi, described above, incubated at 37° C for 2 days, respectively, and examined for the presence of growth, it may be shown that 2-(p-chlorophenyl)-4-isopropyl-6-[1-(naphthalenyloxymethyl)]-2-morpholinol hydrochloride is able to inhibit growth totally in this system of *Candida albicans* and *Trichophytol granulosum* at a concentration of 32 mcg/ml or less.

When the compounds of formula I are used as antifungal agents they may be formulated and administered in the same manner as described hereinbefore for their use as β-receptor blocking agents.

Processes

For the preparation of the 2-morpholinol derivatives of formula I the preferred starting materials are the compounds of general formula II, $$R^1OCH_2CH(OH)CH_2NHR^2 \qquad (II)$$

in which $R^1$ and $R^2$ are as defined in the first instance.

The starting materials of formula II are known, for example, 1-(isopropylamino)-3-(1-naphthalenyloxy)-2-propanol, described in U.S. Pat. No. 3,337,628, encorporated herein by reference, or they may be obtained by the condensation of a compound of formula

in which $R^1$ is as defined herein with an amine of formula $R^2NH_2$ in which $R^2$ is as defined herein, according to the conditions described in the above Belgian Patent.

For the preparation of the 2-morpholinol derivatives of this invention of formula I in which $R^4$ is hydrogen and $R^1$, $R^2$ and $R^3$ are as defined in the first instance, the following process is both practical and convenient:

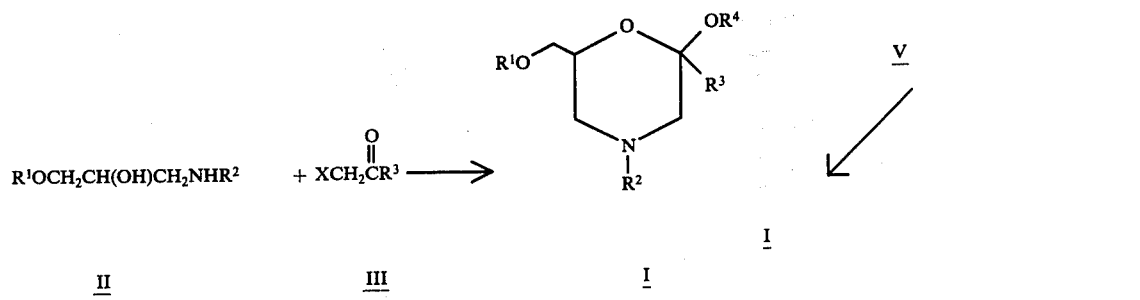

in which $R^4$ is hydrogen, X is halogen selected from chlorine, bromine or iodine and $R^1$, $R^2$ and $R^3$ are as defined in the first instance.

With reference to the above scheme the starting material of formula II is condensed with an α-halocarbonyl compound of formula III in the presence of an alkali metal base to yield the corresponding compounds of formula I in which $R^4$ is hydrogen and $R^1$, $R^2$ and $R^3$ are as defined herein.

In practising the condensation (II + III → I) it is preferable to use a solvent as a reaction medium. Any solvent inert to the reaction conditions may be used. Suitable solvents include benzene, toluene, diethyl ether, dioxane, tetrahydrofuran, methylene dichloride, carbon tetrachloride and the like. Benzene and toluene are especially convenient and practical for this use. A variety of suitable bases can be used for this condensation, for example, the preferred bases include the hydroxide, carbonate and bicarbonate of an alkali metal, preferably sodium or potassium. The amount of base used is not especially critical and may range from 1.1 molar equivalents to 10 molar equivalents; however, a range of from 1.1 to 3 molar equivalents is generally preferred. In addition, a catalytic amount of sodium or potassium iodide, preferably 0.1 to 1.0 molar equivalents, may optionally be added to the reaction mixture. The time of the reaction may range from 5 hours to 10 days, with the preferred range being from 10 to 60 hours. The temperature of the reaction may range from 0° C to the boiling point of the reaction mixture. Preferred temperature ranges include 50° to 120° C.

The α-halocarbonyl compounds of formula III are either known, for example, 2-bromo-4-chloro-acetophenone and chloro-2-propanone, or they may be prepared by known methods described in general organic chemistry textbooks. For example, a comprehensive review on the properties and preparation of such α-haloketones and α-haloaldehydes may be found in "Rodd's Chemistry of Carbon Compounds," S. Coffey, Ed., Vol 1c, 2nd ed., Elsevier Publishing Co., Amsterdam, London and New York, 1965, pp 1–91.

Alternatively, the compound of formula I in which $R^1$, $R^2$, $R^3$ and $R^4$ are as defined in the first instance may be prepared by the following process:

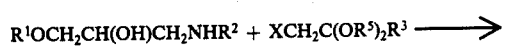

II      IV

V

I in which $R^1$, $R^2$, $R^3$ and $R^4$ are as defined in the first instance, $R^5$ is lower alkyl and X is halogen selected from chlorine, bromine or iodine.

With reference to this alternative process a starting material of formula II is condensed with the compound of formula IV in the presence of a suitable alkali metal base according to the conditions described above for the condensation (II + III → I) to give the corresponding compound of formula V in which $R^1$, $R^2$ and $R^3$ are as defined herein and $R^5$ is lower alkyl. The compounds of formula IV are either known, for example, bromoacetaldehyde diethylacetal, or may be prepared by known methods, for instance, see "Rodd's Chemistry of the Carbon Compounds," cited above. Cyclization of the compound of formula V with an aqueous mineral acid, preferably hydrochloric acid, sulfuric acid or phosphoric acid, in the presence of an organic solvent, for example, an organic solvent selected from those described above for the condensation, affords the corresponding alcohol of formula I in which $R^1$, $R^2$ and $R^3$ are as defined herein and $R^4$ is hydrogen. The time of the latter reaction may range from 10 minutes to 10 hours, preferably from 15 minutes to 2 hours. The temperature of the reaction may range from 20° C to the boiling point of the reaction mixture, preferably from 50° to 120° C.

Alternatively, the intermediate of formula V is cyclized under anhydrous conditions with a suitable anhydrous mineral acid, for example, those described immediately above, in an inert organic solvent, preferably methanol, ethanol, benzene, toluene or a mixture thereof, using reaction times and temperatures as described for the latter described cyclization to obtain the corresponding compound of formula I in which R¹, R² and R³ are as defined herein and R⁴ is lower alkyl.

The above described processes are followed to prepare other compounds of formula I in which R¹ is an aryl radical selected from the group consisting of

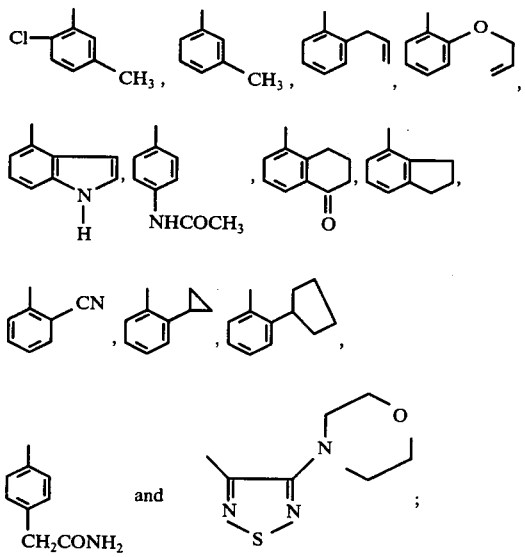

and R², R³ and R⁴ are as defined herein by employing the corresponding compound of formula II with respect to R¹.

The following examples illustrate further this invention.

EXAMPLE 1

2-(p-Chlorophenyl)-4-isopropyl-6-[1-(naphthalenyloxymethyl)]-2-morpholinol hydrochloride (I; R¹ = 1-naphthalenyl, R² = CH(CH₃), R³ = p-chlorophenyl and R⁴ = H)

The starting material of formula II, 1-(isopropylamino)-3-(1-naphthalenyloxy)-2-propanol, (4.6 g, 0.018 mole) and the compound of formula III, 2-bromo-4′-chloro-acetophenone (4.7 g, 0.020 mole), are dissolved in 35 ml of benzene. A solution of 2 g of sodium hydrogen carbonate and 0.2 g of sodium sulphite in 15 ml of water is added. The reaction mixture is stirred at 80° C for 20 hours. The aqueous phase is separated and discarded. The organic phase is washed with 1 ml of 2 M aqueous hydrochloric acid and water, dried over sodium sulfate and evaporated to give the free base of the title compound as an oil, nmr (CDCl₃) δ 1.1 (d, J = 6Hz, 6H), 2.2–3.3 (m, 5H), 4.0–4.85(m, 3H) and 6.8–8.4 (m, 11H). The oil is dissolved in benzene and 8.0 ml of a 2.3M solution of hydrogen chloride in ether is added.

The oil that formed is crystallized from methanol-ether to give the title compound, mp 149°–150° C.

EXAMPLE 2

4-isopropyl-2-methyl-6-[1-(naphthalenyloxymethyl)]-2-morpholinol p-toluenesulfonate (I; R¹ = 1-naphthalenyl, R² = CH(CH₃)₂, R³ = CH₃ and R⁴ = H)

The starting material of formula II, 1-(isopropylamino)-3-(1-naphthalenyloxy)-2-propanol (4.6 g, 0.018 mole), and the compound of formula III, chloropropanone (1.5 ml), are dissolved in 35 ml of toluene. A solution of sodium hydrogen carbonate (2.0 g) and sodium sulphite (0.2 g) in water (15 ml) is added. The reaction mixture is stirred at 80° C for 20 hours. Potassium iodide (0.4 g) and chloropropanone (1 ml) are added and the reaction mixture is heated at reflux for 3 hours. The aqueous phase is separated and discarded. The organic phase is washed with 1 ml of 2 M aqueous hydrochloric acid and water, dried over sodium sulfate and filtered. The organic phase is evaporated and the residue is subjected to chromatography on silica gel using acetone-benzene (3:7) as eluant. The eluate is evaporated to give the free base of the title compound, nmr (CDCl₃) δ 1.00 (d, J = 6.5Hz, 6H), 1.40 (S, 3H), 4.05 (broad S, 1H) and 6.7 – 8.4 (m, 7H). The residue is dissolved in ether and p-toluenesulfonic acid is added. The precipitate is collected and recrystallized from ethanol-methylene dichloride-ether to obtain the title compound, mp 146°–150° C.

In the same manner but replacing the above starting material of formula II with other starting materials of formula II in which R¹ is 1-naphthalenyl and R² is as defined herein and replacing the above starting material of formula III with other starting materials of formula III then other compounds of formula I in which R¹ is 1-naphthalenyl, R² and R³ are as defined herein and R⁴ is hydrogen are obtained. Examples of the latter compounds of formula I are 2-propyl-4-methyl-6-[1-(naphthalenyloxymethyl)]-2-morpholinol, 2-phenyl-4-(1,1-dimethylpropyl)-6-[1-(naphthalenyloxymethyl)]-2-morpholinol, 2-(3-bromophenyl)-4-(1,1-dimethyl-2-propynyl)-6-[1-(naphthalenyloxymethyl)]-2-morpholinol, 2-(3-methylbutyl)-4-ethynyl-6-[1-(naphthalenyloxymethyl)]-2-morpholinol and 2-(2-iodophenyl)-4-(4-methylpentyl)-6-[1-(naphthalenyloxymethyl)]-2-morpholinol.

The procedures of Examples 1 or 2 may be followed to prepare other compounds of formula I in which R¹ is an aryl radical other than 1-naphthalenyl, R² and R³ are as defined in the first instance and R⁴ is hydrogen. Examples of such compounds are listed in Table I. In each of these examples an equivalent amount of the appropriate starting materials of formula II and formula III listed therein are used instead of the starting materials of formula II and formula III described in the procedures of Examples 1 and 2.

TABLE I

| | | | α-halocarbonyl of formula III | | Product:[(prefix listed below)-2-morpholinol] |
|---|---|---|---|---|---|
| | Starting material of Formula II | | | | |
| EX. | R¹ | R² | X | R³ | PREFIX |
| 3 | Cl—⟨phenyl⟩—CH₃ | C₂H₅ | Cl | CH₂CH(CH₃)₂ | 2-(2-methylpropyl)-4-ethyl-6-(2-chloro-5-methylphenyloxymethyl) |

TABLE I-continued

| EX. | Starting material of Formula II R¹ | R² | α-halocarbonyl of formula III X R³ | Product:[(prefix listed below)-2-morpholinol] PREFIX |
|---|---|---|---|---|
| 4 | 3-methylphenyl | $CH_2C{\equiv}CH$ | Br  (2-iodophenyl) | 2-(2-iodophenyl)-4-(2-propynyl)-6-(3-methylphenyloxymethyl) |
| 5 | 2-(2-propenyl)phenyl | $CH_3$ | Br  $C_2H_5$ | 2-ethyl-4-methyl-6-[2-(2-propenylphenyloxymethyl)] |
| 6 | 2-(2-propenyloxy)phenyl | $C_2H_5$ | Br  (phenyl) | 2-phenyl-4-ethyl-6-[2-(2-propenyloxyphenyloxymethyl)] |
| 7 | 4-indolyl | $CH(CH_3)_2$ | Br  $CH_3$ | 2-methyl-4-(1-methylethyl)-6-(4-indolyloxymethyl) |
| 8 | 4-acetylaminophenyl | $n\text{-}C_5H_{11}$ | Cl  (3-fluorophenyl) | 2-(3-fluorophenyl)-4-pentyl-6-(4-acetylaminophenyloxymethyl) |
| 9 | 1-(5,6,7,8-tetrahydronaphthal-5-onyl) | $C{\equiv}CH$ | Cl  $n\text{-}C_5H_{11}$ | 2-pently-4-ethynyl-6-[1-(5,6,7,8-tetrahydronaphthal-5-oneyloxymethyl)] |
| 10 | 7-(2,3-dihydro-1H-indenyl) | $t\text{-}C_4H_9$ | Br  (4-bromophenyl) | 2-(4-bromophenyl)-4-(tert-butyl)-6-[7-(2,3-dihydro-1H-indenyloxymethyl)] |
| 11 | 2-cyanophenyl | $CH_3$ | Br  (phenyl) | 2-phenyl-4-methyl-6-(2-cyanophenyloxymethyl) |
| 12 | 2-cyclopropylphenyl | $C{\equiv}CCH_3$ | Br  $n\text{-}C_6H_{13}$ | 2-hexyl-4-(1-propynyl)-6-(2-cyclopropylphenyloxymethyl) |
| 13 | 2-cyclopentylphenyl | $C(CH_3)_2C{\equiv}CH$ | Cl  $CH(CH_3)_2$ | 2-(1-methylethyl)-4-(1,1-dimethyl-2-propynyl)-6-(2-cyclopentylphenyloxymethyl) |
| 14 | 4-aminocarbonylmethylphenyl | $C(CH_3)CH_2CH_3$ | Br  $C_2H_5$ | 2-ethyl-4-(1,1-dimethylpropyl)-6-(4-aminocarbonylmethylphenyloxymethyl) |

TABLE I-continued

| | Starting material of Formula II | | α-halocarbonyl of formula III | | Product:[(prefix listed below)-2-morpholinol] |
|---|---|---|---|---|---|
| EX. | R¹ | R² | X | R³ | PREFIX |
| 15 | 3-methyl-4-(morpholin-4-yl)-1,2,5-thiadiazole | $C_2H_5$ | I | 2-chlorophenyl | 2-(2-chlorophenyl)-4-ethyl-6-[3-(4-morpholinyl-1,2,5-thiadiazolyloxymethyl)] |
| 16 | 3-methyl-4-(morpholin-4-yl)-1,2,5-thiadiazole | C≡CH | Br | $CH_2CH(CH_3)_2$ | 2-(2-methylpropyl)-4-ethynyl-6-[3-(4-morpholinyl-1,2,5-thiadiazolyloxymethyl)] |
| 17 | 4-($CH_2CONH_2$)phenyl | $CH_2C≡CH$ | Cl | 2-bromophenyl | 2-(2-bromophenyl)-4-(2-propynyl)-6-(4-aminocarbonylmethylphenyloxymethyl) |
| 18 | 2-cyclopentylphenyl | $CH(CH_3)_2$ | Br | 4-chlorophenyl | 2-(4-chlorophenyl)-4-(1-methylethyl-6-(2-cyclopentylphenyloxymethyl) |
| 19 | 2-cyclopropylphenyl | $CH_3$ | Cl | phenyl | 2-phenyl-4-methyl-6-(2-cyclopropylphenyloxymethyl) |
| 20 | 2-cyanophenyl | C≡CH | Cl | $C_2H_5$ | 2-ethyl-4-ethynyl-6-(2-cyanophenyloxymethyl) |
| 21 | 2,3-dihydro-1H-indenyl | $CH_2C≡CH$ | Cl | $CH_2CH(CH_3)_2$ | 2-(2-methylpropyl)-4-(2-propynyl)-6-[7-(2,3-dihydro-1H-indenyloxymethyl)] |
| 22 | 5,6,7,8-tetrahydronaphthal-5-onyl | n-$C_6H_{13}$ | Br | 3-iodophenyl | 2-(3-iodophenyl)-4-hexyl-6-[1-(5,6,7,8-tetrahydronaphthal-5-oneyloxymethyl)] |
| 23 | 4-(NHCOCH₃)phenyl | C≡CCH₃ | Cl | $CH_3$ | 2-methyl-4-(1-propynyl)-6-(4-acetylaminophenyloxymethyl) |
| 24 | indolyl | $C(CH_3)_2C≡CH$ | Cl | phenyl | 2-phenyl-4-(1,1-dimethyl-2-propynyl)-6-(4-indolyloxymethyl) |
| 25 | 2-allyloxyphenyl | $CH_2CH_2C≡CH$ | Cl | n-$C_5H_{11}$ | 2-pentyl-4-(3-butynyl)-6-[2-(2-propenylxyphenyloxymethyl)] |

TABLE I-continued

| EX. | Starting material of Formula II R¹ | R² | α-halocarbonyl of formula III X | R³ | Product:[(prefix listed below)-2-morpholinol] PREFIX |
|---|---|---|---|---|---|
| 26 | 2-allylphenyl | C≡CH | Cl | 4-iodophenyl | 2-(4-iodophenyl)-4-ethynyl-6-[2-(2-propenylphenyloxymethyl)] |
| 27 | 3-methylphenyl | n-C₄H₉ | Cl | CH(CH₃)₂ | 2-(1-methylethyl)-4-butyl-6-(3-methylphenyloxymethyl) |
| 28 | 4-chloro-3-methylphenyl | CH₂C≡CH | Br | 2-fluoro-5-methylphenyl | 2-(2-fluorophenyl)-4-(2-propynyl)-6-(2-chloro-5-methylphenyloxymethyl) |

EXAMPLE 29

1-[(2,2-Diethoxyethyl)(1-methylethyl)amino]-3-(1-naphthalenyloxy)-2-propanol(V; R¹ = 1-naphthalenyl, R² = CH(CH₃)₂, R³ = H and R⁵ = CH₂CH₃)

To the starting material of formula II, 1-(isopropylamino)-3-(1-naphthalenyloxy)-2-propanol, as the hydrochloride (5.2 g, 0.018 mole), and the compound of formula IV, bromoacetaldehyde diethylacetal (3.6 g, 0.018 mole), in benzene (35 ml), a solution of sodium hydrogen carbonate (4.0 g, 0.048 mol) and sodium bisulfite (0.2 g) in water (25 ml) is added. The reaction mixture is stirred at 80° C for 20 hours. Potassium iodide (0.8 g) and xylene (30 ml) are added and the reaction mixture is heated at reflux for 6 days during which time a total of 5 ml of bromoacetaldehyde diethylacetal is added portionwise. After cooling, the aqueous phase is separated and discarded. The organic layer is dried, filtered and evaporated to dryness to afford an oily residue which is subjected to chromatography on silica gel using a 15% acetone-benzene mixture as eluant. The eluate is evaporated to obtain the title compound as an oil, nmr (CDCl₃) δ 0.99 and 1.09 (doublets, J = 3Hz, 6H), 1.2 (t, J = 7Hz, 6H), 2.6–3.1(m, 5H), 3.25–3.9(m, 5H), 4.0–4.65 (m, 4H) and 6.75–8.4 (m, 7H).

In the same manner but replacing the above starting material of formula II with other starting materials of formula II in which R¹ is 1-naphthalenyl and R² is as defined herein and replacing the above starting material of formula IV with other compounds of formula IV then other compounds of formula V in which R¹ is 1-naphthalenyl and R², R³ and R⁵ are as defined herein are obtained. Examples of the latter compounds of formula V are 1-[(2,2-dimethoxyethyl)(ethyl)amino]-3-(1-naphthalenyloxy)-2-propanol, 1-[(2,2-dipropoxypropyl)(1,1-dimethylethyl)-amino]-3-(1-naphthalenyloxy)-2-propanol and 1-[(2,2-diethoxyethyl)(1,1-dimethyl-2-propynyl)amino]-3-(1-naphthalenyloxy)-2-propanol.

EXAMPLE 30

2-Ethoxy-4-(1-methylethyl)-6-[1-(naphthalenyloxymethyl)]-morpholine (1; R¹ = 1-naphthalenyl, R² = CH(CH₃)₂, R³ = H and R⁴ = CH₂CH₃)

The compound of formula V, 1-[(2,2-diethoxyethyl)(1-methylethyl)-amino]-3-(1-naphthalenyloxy)-2-propanol, described in Example 29, (0.015 g) in benzene (1 ml) and ethanol (1 ml) saturated with anhydrous hydrogen chloride is heated at reflux temperature for one hour. The solution is cooled, made alkaline with 10% aqueous sodium hydroxide and extracted with ether. The organic phase is dried and evaporated to give the title compound as an oil, $\gamma_{max.}^{CHCl_3}$ 1580, 1000, 790 and 770 cm⁻¹.

In the same manner but replacing the above starting material of formula V with other starting materials of formula V, for instance those described in Example 29, then other compounds of formula I in which R¹ is 1-naphthalenyl, R² and R³ are as defined herein and R⁴ is lower alkyl are obtained. Examples of the latter compunds of formula I are 2-methoxy-4-ethyl-6-[1-(naphthalenyloxymethyl)]-morpholine, 2-propoxy-2-methyl-4-(1,1-dimethylethyl)-6-[1-(naphthalenyloxymethyl)]-morpholine and 2-ethoxy-4-(1,1-dimethyl-2-propynyl)-6-[1-(naphthalenyloxymethyl)]-morpholine.

EXAMPLE 31

4-(1-Methylethyl)-6-[1-naphthalenyloxymethyl)]-2-morpholinol (1; R¹ = 1-naphthalenyloxy, R² = CH(CH₃)₂, R³ and R⁴ = H)

The compound of formula V, 1-[(2,2-diethoxyethyl)(1-methylethyl)-amino]-3-(1-naphthalenyloxy)-2-propanol, described in Example 29, (0.015 g) in 6N hydrochloric acid (1 ml) is heated at reflux temperature for 30 min. The solution is cooled, made alkaline with 10% sodium hydroxide and extracted with ether. The organic phase is dried and evaporated to give the title compound as an oil, Rf = 0.35 on silica gel plates using 30% acetone in benzene.

In the same manner but replacing the above starting material of formula V with other starting materials of formula V, for instance those described in Example 29, then other compounds of formula I in which R¹ is 1-naphthalenyl, R² and R³ are as defined herein and R⁴ is hydrogen are obtained. Examples of the latter compounds of formula I are 4-ethyl-6-[1-(naphthalenyloxymethyl)]-2-morpholinol, 4-(1,1-dimethylethyl)-2-methyl-6-[1-(naphthalenyloxymethyl)]-2-morpholinol and 4-(1,1-dimethyl-2-propynyl)-6-[1-(naphthalenyloxymethyl)]-2-morpholinol.

The procedure of Example 29 may be followed to prepare other intermediates of formula V. Said intermediates of formula V thus obtained are further reacted according to the procedure of Example 30 or Example 31 to prepare other compounds of formula I in which $R^1$ is an aryl radical other than 1-naphthalenyl and $R^2$, $R^3$ and $R^4$ are as defined in the first instance. Examples of such compounds are listed in Table II. In each of these examples an equivalent amount of the starting materials of formula II and formula IV listed therein are used instead of the starting materials of formula II and formula IV described in the procedure of Example 29.

TABLE II

| | Starting material of formula II | | Starting material of formula IV | | | Product:[(prefix listed below) except where -2-morpholinol specified] |
|---|---|---|---|---|---|---|
| EX. | $R^1$ | $R^2$ | X | $R^3$ | $R^5$ | PREFIX |
| 31 | 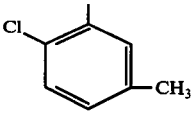 | $C(CH_3)_2CH_2CH_3$ | Br | $n$-$C_3H_7$ | $C_2H_5$ | 2-ethoxy-2-propyl-4-(1,1-dimethylpropyl)-6-(2-chloro-5-methylphenyloxymethyl) and |
| | | | | | | 2-propyl-4-(1,1-dimethylpropyl)-6-(2-chloro-5-methylphenyloxy-methyl)-2-morpholinol |
| 32 | 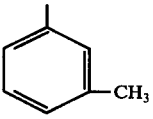 | $CH_3$ | Br | $C_2H_5$ | $C_2H_5$ | 2-ethoxy-2-ethyl-4-methyl-6-(3-methylphenyloxymethyl) and |
| | | | | | | 2-ethyl-4-methyl-6-(3-methylphenyloxymethyl)-2-morpholino |
| 33 | 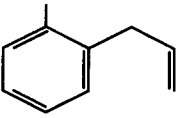 | $CH_2CH_2C\equiv CH$ | Cl | $CH_3$ | $n$-$C_3H_7$ | 2-propoxy-2-methyl-4-(3-butynyl)-6-[2-(2-propenylphenyloxymethyl)] |
| 34 | 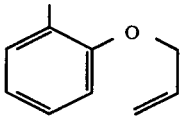 | $CH(CH_3)_2$ | Cl | $C_2H_5$ | $CH_3$ | 2-methoxy-2-ethyl-4-(1-methylethyl)-6-[2-(2-propenyloxy-phenyloxymethyl)] |
| 35 | 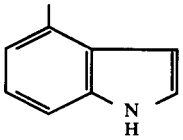 | $C(CH_3)_2C\equiv CH$ | Cl | H | $CH_3$ | 2-methoxy-4-(1,1-dimethyl-2-propynyl)-6-(4-indolyloxymethyl)-2-morpholinol and |
| | | | | | | 4-(1,1-dimethyl-2-propynyl)-6-(4-indolyloxymethyl) |
| 36 | 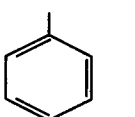 | $C_2H_5$ | Cl | H | $C_2H_5$ | 2-ethoxy-4-ethyl-6-(4-acetylaminophenyloxymethyl) |
| 37 | 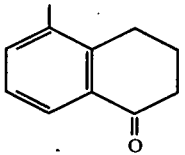 | $n$-$C_3H_7$ | Cl | H | $C_2H_5$ | 2-ethoxy-4-propyl-6-[1-(5,6,7,8-tetrahydronaphthal-5-oneyloxymethyl)] and |
| | | | | | | 4-propyl-6-[1-(5,6,7,8-tetrahydronaphthal-5-oneyloxymethyl)]-2-morpholinol |
| 38 | 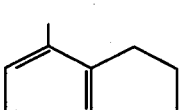 | $CH(CH_3)_2$ | Br | H | $CH_3$ | 2-methoxy-4-(1-methylethyl)-6-[7-(2,3-dihydro-1H-indenyloxymethyl)] -2-morpholinol and |
| | | | | | | 4-(1-methylethyl)-6-[7-(2,3-dihydro-1H-indenyloxymethyl)] |
| 39 | 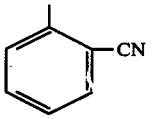 | $C(CH_3)_2CH_2CH_3$ | Br | H | $C_2H_5$ | 2-ethoxy-4-(1,1-dimethylpropyl)-6-(2-cyanophenyloxymethyl)-2-morpholinol and |
| | | | | | | 4-(1,1-dimethylpropyl)-6- |

TABLE II-continued

| EX. | Starting material of formula II R¹ | R² | Starting material of formula IV X | R³ | R⁵ | Product:[(prefix listed below) except where -2-morpholinol specified] PREFIX |
|---|---|---|---|---|---|---|
| 40 | 2-cyclopropylphenyl (o-cyclopropyl methylphenyl) | n-C₆H₁₃ | Br | H | n-C₃H₇ | (2-cyanophenyloxymethyl) 2-propoxy-4-hexyl-6-(2-cyclopropylphenyloxymethyl) and 4-hexyl-6-(2-cyclopropylphenyloxymethyl)-2-morpholinol |
| 41 | 2-cyclopentylphenyl (o-cyclopentyl methylphenyl) | CH₃ | Cl | CH₃ | C₂H₅ | 2-ethoxy-2, 4-dimethyl-6-(2-cyclopentylphenyloxymethyl)-2-morpholinol and 2,4-dimethyl-6-(2-cyclopentylphenyloxymethyl) |
| 42 | 4-(CH₂CONH₂)phenyl | C₂H₅ | Cl | H | C₂H₅ | 2-ethoxy-4-ethyl-6-(4-aminocarbonylmethylphenyloxymethyl)-2-morpholinol and 4-ethyl-6-(4-aminocarbonylmethyl)-2-morpholinol |
| 43 | 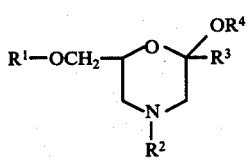 | n-C₅H₁₁ | Cl | H | n-C₄H₉ | 2-butoxy-4-pentyl-6-[3-(4-morpholinyl-1,2,5-thiadiazolyloxymethyl)] and 4-pentyl-6-[3-(4-morpholinyl-1,2,5-thiadiazolyloxymethyl)]-2-morpholinol |

We claim:
1. A compound of formula I

$$R^1-OCH_2-\underset{\underset{R^2}{|}}{\overset{O}{\diagup}}\overset{OR^4}{\underset{R^3}{\diagdown}}$$ (1)

in which R¹ is 1-naphthalenyl; R² is selected from the group consisting of lower alkyl and lower alkynyl; R³ is selected from the group consisting of hydrogen, lower alkyl, phenyl and phenyl substituted with a halo; and R⁴ is selected from the group consisting of hydrogen and lower alkyl; or therapeutically acceptable salt thereof.

2. 2-(p-Chlorophenyl)-4-isopropyl-6-[1-(naphthalenyloxymethyl)]-2-morpholinol, as claimed in claim 1.

3. 4-Isopropyl-2-methyl-6-[1-(naphthalenyloxymethyl)]-2-morpholinol, as claimed in claim 1.

4. 2-Ethoxy-4-(1-methylethyl)-6-[1-(naphthalenyloxymethyl)]-morpholine, as claimed in claim 1.

5. 4-(1-Methylethyl)-6-[1-(naphthalenyloxymethyl)]-2-morpholinol, as claimed in claim 1.

6. A β-adrenergic or anti-fungal composition comprising an effective amount of a compound of formula I, or a therapeutically acceptable salt thereof as defined in claim 1, and a pharmaceutically acceptable carrier.

7. A method for treating heart diseases in a mammal which is amenable to treatment with a β-adrenergic blocking agent which comprises administering to said mammal of an effective amount of a β-adrenergic blocking compound selected from those of formula I, or a therapeutically acceptable salt thereof, as claimed in claim 1.

8. A method for treating fungal infections in a mammal which comprises administering to said mammal of an effective amount of a compound selected from those of formula I, or a therapeutically acceptable salt thereof, as claimed in claim 1.

* * * * *

UNITED STATES PATENT AND TRADEMARK OFFICE
CERTIFICATE OF CORRECTION

PATENT NO. : 4,044,131
DATED : August 23, 1977
INVENTOR(S) : Andre A. Asselin and Leslie G. Humber It is certified that error appears in the above-identified patent and that said Letters Patent are hereby corrected as shown below:

Column 3, line 56, for "or" read - -of- -.

Column 4, line 66, for "encor-" read - -incor- - -.

Column 7, line 40 for "$CH(CH_3)$" read - -$CH(CH_3)_2$ - -.

Column 9, line 63, Example 14, for "$C(CH_3)CH_2CH_3$" read - -$C(CH_3)_2CH_2CH_3$- -.

Column 10, line 35, for "2-pently" read - -2-pentyl- -.

Column 13, line 24, for "aminol-3-(1-" read - -amino]-3-(1- - -.

Column 16, line 9, Table II, right column, first heading, for "below) except" read - -below)morpholine except - -.

Column 16, line 24, Table II, right column, Example 32, for "2-morpholino" read - - 2-morpholinol - -.

Column 18, line 3, Table II; right column, first heading, for "below) except" read - - below)morpholine except - -.

Signed and Sealed this

Twentieth Day of June 1978

[SEAL]

Attest:

RUTH C. MASON
*Attesting Officer*

DONALD W. BANNER
*Commissioner of Patents and Trademarks*